United States Patent [19]

LeBlanc et al.

[11] Patent Number: 4,990,162

[45] Date of Patent: Feb. 5, 1991

[54] ROTARY HAND PROSTHESIS

[75] Inventors: Maurice LeBlanc, Redwood City, Calif.; Lawrence Carlson, Boulder; Carib Nelson, Denver, both of Colo.

[73] Assignee: Children's Hospital at Stanford, Palo Alto, Calif.

[21] Appl. No.: 397,328

[22] Filed: Aug. 22, 1989

Related U.S. Application Data

[63] Continuation of Ser. No. 170,489, Mar. 21, 1988, abandoned.

[51] Int. Cl.⁵ .......................... A61F 2/54; A61F 2/68
[52] U.S. Cl. ...................................... 623/63; 623/57; 901/39
[58] Field of Search ............. 414/1, 7; 623/52, 63–65, 623/62, 57; 901/21, 30, 39; 294/104, 106, 19.1, 22, 23

[56] References Cited

U.S. PATENT DOCUMENTS

| | | | |
|---|---|---|---|
| 728,941 | 5/1903 | Lanham | 294/22 |
| 1,247,077 | 11/1917 | Caron | 623/65 X |
| 2,482,555 | 9/1949 | Otterman | 623/62 |
| 2,532,732 | 12/1950 | Sansbury | 623/57 |
| 2,535,489 | 12/1950 | Edwards | 623/63 |
| 2,847,678 | 8/1958 | Opuszenski | 623/64 |
| 3,866,966 | 2/1975 | Skinner, II | 623/64 X |
| 3,901,547 | 8/1975 | Skinner, II | 294/106 X |
| 4,623,183 | 11/1986 | Aomori | 294/106 X |

FOREIGN PATENT DOCUMENTS

| | | | |
|---|---|---|---|
| 0529546 | 8/1956 | Canada | 623/63 |
| 1019129 | 1/1953 | France | 294/22 |
| 0011456 | 2/1978 | Japan | 623/64 |
| 7014761 | 4/1971 | Netherlands | 623/63 |
| 0572358 | 10/1945 | United Kingdom | 623/57 |

OTHER PUBLICATIONS

Prosthetic Principles Upper Extremity Amputations Fabrication and Fitting Principles, published by Prosthetics-Orthotics Education Program—Division of Orthopedic Surgery, University of California, Los Angeles (Chapter 3 Components).

12 pages—Hosmer Dorrance Corporation catalog, Upper Extremity Prosthetic Components.

*Primary Examiner*—Ronald Frinks
*Assistant Examiner*—David H. Willse
*Attorney, Agent, or Firm*—Townsend and Townsend

[57] ABSTRACT

The present invention is a prosthetic prehensor with two members extending in the same direction. One of the members rotates about a parallel axis removed from the first member until it contacts the first member. In the preferred embodiment, the two members are curved plates, one simulating a thumb and the other being wider and simulating a palm. The thumb plate rotates around a base plate which is coupled to the end of an arm. The thumb plate can contact the palm plate in either of two directions. This allows two types of gripping for fine objects and larger objects. The use of plates that are curved allows for a more aesthetic design than metal hooks.

15 Claims, 3 Drawing Sheets

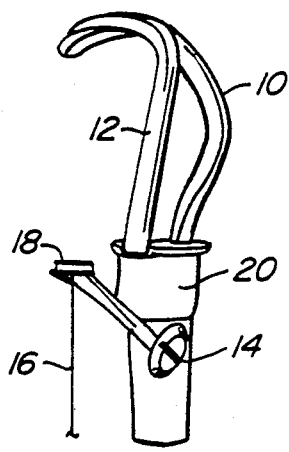
FIG._1.
PRIOR ART
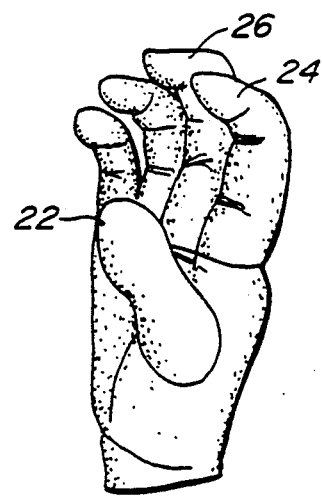
FIG._2.
PRIOR ART
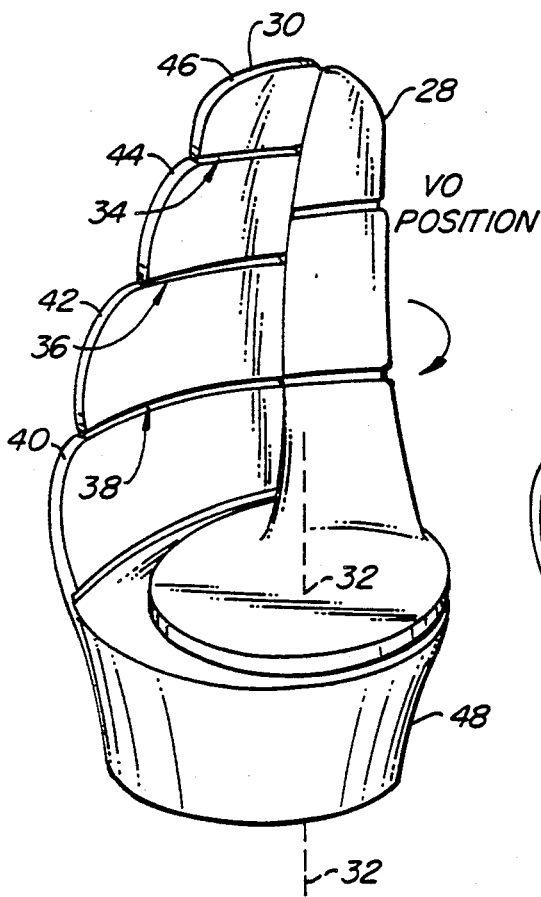
FIG._3.
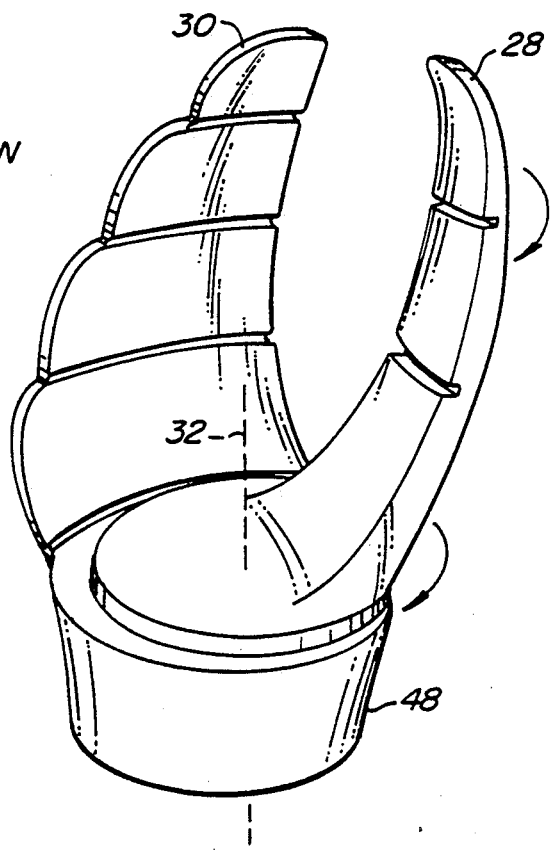
FIG._4.

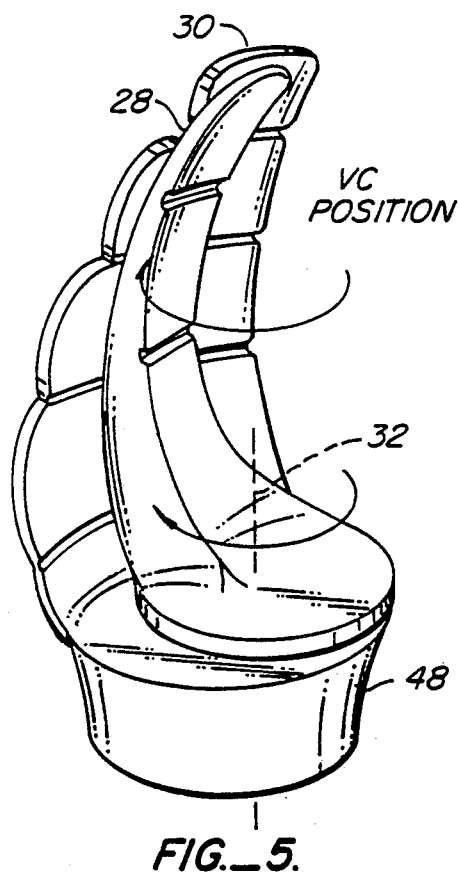
FIG._5.
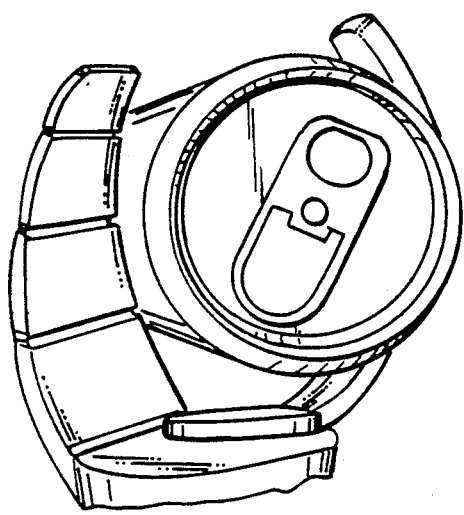
FIG._6.
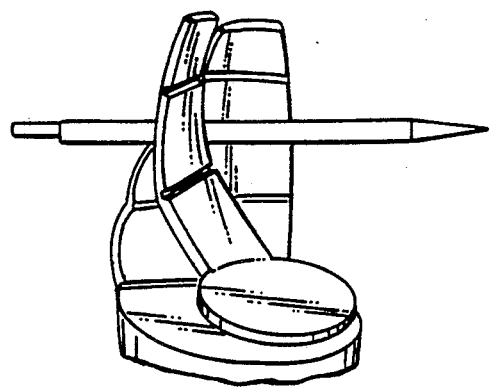
FIG._7.

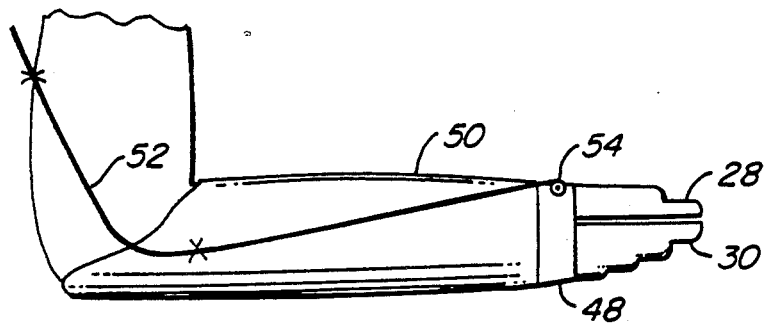
FIG._8.
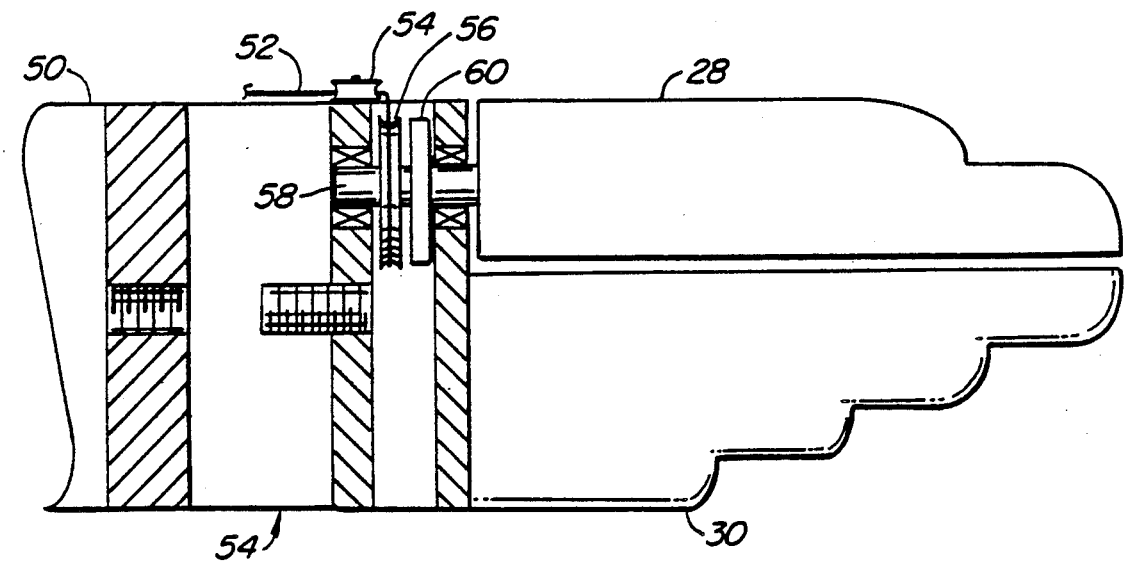
FIG._9.

ROTARY HAND PROSTHESIS

This invention was made partially with government support under Field-Initiated Grant No. 133MH70021 from the National Institute on Disability Rehabilitation and Research, U.S. Department of Education.

This is a continuation of application Ser. No. 07/170,489, filed Mar. 21, 1988, now abandoned.

BACKGROUND

The present invention relates to a hand prosthesis or prosthetic prehensor for use by an amputee.

At the present time, arm amputees have a basic choice of a hook or an artificial hand for the prosthetic prehensor. There are compromises between these two options. The hook is more functional, and the hand is more cosmetic.

A typical hook is shown in FIG. 1. The hook has two hook bars 10 and 12. Hook bar 10 is stationary while hook bar 12 is moved about a pivot 14 by a cable 16 pulling on a member 18. Cable 16 is typically attached to a harness to the amputee's shoulder, and the hook is opened by shrugging the shoulder. The hook shown is the voluntary opening (VO) type, and is closed by the action of a spring in the form of a resilient band 20. Other types of prosthetic prehensors may be of the voluntary closing (VC) type. The VC type is more mechanically complex and less frequently used. The hook of FIG. 1 has the advantages that it is light weight, the object being grasped can be seen, the construction is mechanically simple, it is compact enough to get into pockets and is versatile.

A second type of hand prothesis is shaped to look like a human hand and does not actually move. A mechanical hand prothesis is shown in FIG. 2. Most mechanical hands are designed with 3- point prehension using a thumb 22, index finger 24 and a middle finger 26. The remaining two fingers are passive and positionable on some hands, and active and move with the index and middle fingers on others. Most mechanical hands have a grip lock to prevent accidental opening when an object is being carried. The hand is opened by pulling a cable in a similar manner to the hook in FIG. 1. The mechanical mechanisms in the hand are typically covered with a PVC foam material which feels similar to human flesh. In addition, a plastic, cosmetic glove is usually worn over the mechanical hand. The hand is more cosmetic in appearance than the hook, but is heavier, makes it more difficult to see the object being grasped, is mechanically more complex, can not get into pockets and is less versatile than the hook.

Motorized or bionic hands also exist, but are more heavy, complicated and expensive.

Some amputees use two prehensors and interchange them, using a hook for work and the hand for social situations. In addition, there are numerous types of hooks designed for specific tasks.

Many upper-limb amputees who have been queried have expressed a desire for a prehensor which functions as well as a hook but is more aesthetic and less conspicuous looking. A more aesthetic looking prehensor need not be in the shape of a hand.

SUMMARY OF THE INVENTION

The present invention, as shown in FIGS. 3-5, is a prosthetic prehensor with two members extending in the same direction. One of the members rotates about a parallel axis removed from the first member until it contacts the first member.

In the preferred embodiment, the two members are curved plates, one simulating a thumb and the other being wider and simulating a palm. The thumb plate rotates around a base plate which is coupled to the end of an arm. The thumb plate can contact the palm plate in either of two directions. This allows two types of gripping for fine objects and larger objects. The use of plates that are curved allows for a more aesthetic design than metal hooks.

The prehensor has the advantages of the metal hook of the prior art in that it is light weight, allows viewing of the object to be grasped, is mechanically simple, and can fit into pockets when the thumb plate is rotated to adjacent the palm plate.

The thumb plate differs from the prior art in two respects. First, it rotates, rather than straight or linear opening and closing, thus requiring motion in a different direction from the prior art. Second, since the thumb plate is mounted at a distance from its axis of rotation, a small movement of a shaft along this axis can cause a large movement of the thumb plate. A two-pulley arrangement is used to attach a normal shoulder harness cable to the rotating thumb plate. The two pulleys act to both translate the direction of motion and to increase the amount of movement of the thumb plate for a given travel distance of the cable as discussed above.

The invention is thus a prosthetic prehensor comprising: a first elongate member; a second elongate member extending in a direction parallel to said first elongate member; and means for rotating said second elongate member about an axis parallel to said first elongate member and removed from said first elongate member so that said second member contacts said first member.

In the preferred embodiment, the present invention is a prosthetic prehensor comprising: a base plate; a curved palm plate fixed to said base plate proximate an edge of said base plate and tapering away from said base plate, said palm plate having a flat edge substantially orthogonal to said base plate, a curved, tapering edge opposite said flat edge, and an inside face between said flat and curved edges facing a center of said base plate; a curved thumb plate movably coupled to said base plate having a flat edge substantially orthogonal to said base plate and a curved, tapering edge opposite said thumb plate edge such that, in a first position, said thumb plate flat edge is opposite said palm plate flat edge, said thumb plate being mounted for rotation about an axis through said base plate, said axis being removed from said palm plate; means for rotating said thumb plate around said axis from a second, closed position where said flat edge of said thumb plate is in contact with said flat edge of said palm plate, through said second position, to a third position where said curved edge of said thumb plate is in contact with said inside face of said palm plate; means for biasing said thumb plate into said second closed position; a cable for activating said means for rotating; and means for translating movement of said cable toward and away from said palm and thumb plates into rotary movement around said axis.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a perspective view of prior art hook prehensor;

FIG. 2 is a perspective view of a prior art hand prehensor;

FIGS. 3-5 are perspective views of the rotary prehensor of the present invention showing different positions of the thumb plate;

FIG. 6 is a perspective view of the prehensor of FIGS. 3-5 grasping a can;

FIG. 7 is a perspective view of the prehensor of FIGS. 3-5 grasping a pencil;

FIG. 8 is a diagram showing the placement of the prehensor on an artificial arm; and FIG. 9 is a diagram of the cable and pulley control system for the prehensor of the FIG. 3.

DETAILED DESCRIPTION OF THE PREFERRED EMBODIMENT

FIG. 3 shows a prehensor according to the present invention with a thumb plate 28 in contact with a palm plate 30. Thumb plate 28 rotates about an axis 32 on a base 48 as shown in FIGS. 4 and 5 until it comes into contact with palm plate 30 from a second direction as shown in FIG. 5. Thumb plate 28 and palm plate 30 are preferably made from a composite plastic, but could be any other material as well.

FIG. 3 shows a VO (voluntary opening) position in which a spring force holds plates 28 and 30 together, and they must be opened by pulling on a cable.

FIG. 5 shows a VC (voluntary close) position in which the cable must be pulled to close plate 28 against plate 30. The VO position of FIG. 3 allows for finger tip grasp and the VC position of FIG. 5 allows palmar grasp.

As can be seen, the prehensor is a somewhat abstract representation of a hand having grooves 34, 36 and 38 which correspond to the inside of the knuckles of the hand. In addition, ridges 40, 42, 44 and 46 correspond to the four fingers of the hand.

The movement of thumb plate 28 roughly mimics the natural movement of the thumb on the hand which basically rotates from an open position for grasping a can, mug, etc. as shown in FIG. 6 to a closed position for grasping a pencil, etc. as shown in FIG. 7.

The design thus allows an object to be held in the VO position of FIG. 3 with no harness pull or an object to be held in the VC position of FIG. 5 with variable prehension proportional to harness pull.

FIG. 8 shows the prehensor of the present invention with its base 48 mounted on a below-elbow artificial arm 50. A cable 52 attaches to a shoulder harness (not shown) and to an idler pulley 54 on base 48 as shown in more detail in FIG. 9.

As can be seen in FIG. 9, the direction of movement of cable 52 is translated between idler pulley 54 and a pulley 56. Pulley 56 is coupled directly to a shaft 58 which is connected to thumb plate 28. A clock spring 60 supplies the spring force for closing thumb 28 against palm 30. By using a pulley 56 with an outside diameter smaller than the distance of the outer edge of thumb plate 28 from shaft 58, the thumb plate can be caused to move a larger distance than the cable is pulled. A gearing arrangement could be added to FIG. 9 to provide even larger variations in the movement of thumb plate 28 relative to the movement of cable 52.

As will be understood by those familiar with the art, the present invention may be embodied in other specific forms without departing from the spirit or essential characteristics thereof. For example, the thumb and palm plates could be shaped differently and an arrangement other than the pulley arrangement of FIG. 9 could be used for moving the thumb plate.

Alternately, the palm could move relative to a stationary thumb. Accordingly, the disclosure of the preferred embodiment of the invention is intended to be illustrative, but not limiting, of the scope of the invention which is set forth in the following claims.

What is claimed is:

1. A prosthetic prehensor for attachment to the end of an arm, comprising:
    a first elongate member extending away from said arm and having a first member far end and edge and palm surfaces between said arm and said far end, said palm surface being substantially wider than said edge surface;
    a second elongate member rotatably coupled to said first elongate member and extending in a direction parallel to said first elongate member and having a second member far end and first and second opposed sides between said arm and said second member far end; and
    means for rotating said second elongate member about an axis removed from said first elongate member in a first direction of rotation so that said first side of said second member contacts said edge surface of said first member and rotating said second elongate member in a second opposite direction of rotation so that said second side of said second member contacts said palm surface of said first member.

2. The prehensor of claim 1 wherein said first member is a first curved plate and said second member is a second curved plate smaller than said first curved plate.

3. The prehensor of claim 2 wherein said plates are tapered toward a remote end of the prehensor.

4. The prehensor of claim 1 further comprising a rotary spring for biasing said second member toward said first member in one direction.

5. The prehensor of claim 4 wherein each of said first and second members have a flat edge and a curved edge and said rotary spring biases said flat edges together.

6. The prehensor of claim 1 further comprising a cable coupled to said means for rotating and means for translating movement of said cable toward or away from said prehensor into rotary movement.

7. The prehensor of claim 6 wherein said means for translating comprises a pair of orthogonal pulleys positioned immediately adjacent each other to bend said cable approximately 90 degrees.

8. A prosthetic prehensor comprising:
    a base plate;
    a curved palm plate fixed to said base plate proximate an edge of said base plate and tapering away from said base plate, said palm plate having a flat edge substantially orthogonal to said base plate, a curved, tapering edge opposite said flat edge, and an inside face between said flat and curved edges facing a center of said base plate;
    a curved thumb plate movably coupled to said base plate having a flat edge substantially orthogonal to said base plate and a curved, tapering edge opposite said thumb plate edge such that, in a first position, said thumb plate flat edge is opposite said palm plate flat edge, said thumb plate being mounted for rotation about an axis through said base plate, said axis being removed from said palm plate;

means for rotating said thumb plate around said axis from said first, closed position where said flat edge of said thumb plate is in contact with said flat edge of said palm plate, through a second position, to a third position where said curved edge of said thumb plate is in contact with said inside face of said palm plate;

means for biasing said thumb plate into said second closed position;

a cable for activating said means for rotating; and means for translating movement of said cable toward and away from said palm and thumb plates into rotary movement around said axis.

9. A prosthetic prehensor for attachment to the end of a human arm, comprising:

a first, fixed elongate member extending away from said arm and having a first member far end and first and second opposed sides between said arm and said far end, and an inside palm surface between said first and second sides, said palm surface being substantially wider than said sides;

a second elongate member rotatably coupled to said first elongate member and extending in a direction parallel to said first elongate member and having a second member far end and first and second opposed sides between said arm and said second member far end; and means for rotating said second elongate member, about an axis removed from said first elongate member, in a first direction of rotation so that said first side of said second member contacts said first side of said first member and rotating said second elongate member in a second, opposite direction of rotation so that said second side of said second member contacts said inside palm surface of said first member.

10. The prehensor of claim 9 wherein said first member is a first curved palm plate and said second member is a second curved thumb plate smaller than said first curved plate.

11. The prehensor of claim 10 wherein said plates are tapered toward a remote end of the prehensor.

12. The prehensor of claim 9 further comprising a rotary spring for biasing said second member toward said first member in one direction.

13. The prehensor of claim 12 wherein each of said first and second members have a flat edge and a curved edge and said rotary spring biases said flat edges together.

14. The prehensor of claim 9 further comprising a cable coupled to said means for rotating and means for translating movement of said cable toward or away from said prehensor into rotary movement.

15. The prehensor of claim 14 wherein said means for translating comprises a pair of orthogonal pulleys positioned immediately adjacent each other to bend said cable approximately 90 degrees.

* * * * *